United States Patent [19]

Sauerwein et al.

[11] Patent Number: 4,631,415

[45] Date of Patent: Dec. 23, 1986

[54] RADIATION TREATMENT APPARATUS

[75] Inventors: Kurt Sauerwein, Bergische Strasse 16, D-5657 Haan 1; Norbert Kinzer; Karl Weinlich, both of Wuppertal, all of Fed. Rep. of Germany

[73] Assignee: Kurt Sauerwein, Haan, Fed. Rep. of Germany

[21] Appl. No.: 654,296

[22] Filed: Sep. 25, 1984

[30] Foreign Application Priority Data

Sep. 30, 1983 [DE] Fed. Rep. of Germany ....... 3335438

[51] Int. Cl.⁴ ................................................. G21F 5/02
[52] U.S. Cl. .............................. 250/497.1; 250/496.1
[58] Field of Search ........................... 250/496.1, 497.1

[56] References Cited

U.S. PATENT DOCUMENTS

| | | | |
|---|---|---|---|
| 3,562,532 | 2/1971 | Santoro et al. | 250/497.1 |
| 3,861,380 | 1/1975 | Chassagne et al. | 250/497.1 |
| 4,150,298 | 4/1979 | Brault et al. | 250/497.1 |
| 4,225,790 | 9/1980 | Parsons et al. | 250/497.1 |
| 4,233,517 | 11/1980 | Van't Hooft | 250/497.1 |

*Primary Examiner*—Bruce C. Anderson
*Attorney, Agent, or Firm*—Martin A. Farber

[57] ABSTRACT

A radiation treatment apparatus comprising a radiation shielding container (a rest container) having a plurality of first openings. A plurality of radiator holders are connected to respective drive cables, the radiator holders being axially insertable and removable from the openings by means of the drive cables through flexible hoses connected to the container at the openings. A common single drive unit is connected to all of the drive cables for joint movement of all the drive cables and therewith for joint insertion and joint removal of the radiator holders into and from the openings via the drive cables. A second radiation shielding container (an intermediate container) has a plurality of second openings for selectively receiving respective of the radiator holders. Hose coupling elements provide detachable through-connections of the free ends of the flexible hoses selectively to a respective one of the second openings or a respective hollow probe for treatment. The drive simultaneously inserts the radiator holders selected for treatment into the respective hollow probes and for simultaneously inserting the radiator holders not selected for treatment into the respective second openings, whereby the radiator holders not required at the time for treatment are guided through the respective flexible hoses into the respective second openings in the second radiation shielding container while the radiation holders required at the time for treatment are guided into the respective hollow probes.

13 Claims, 12 Drawing Figures

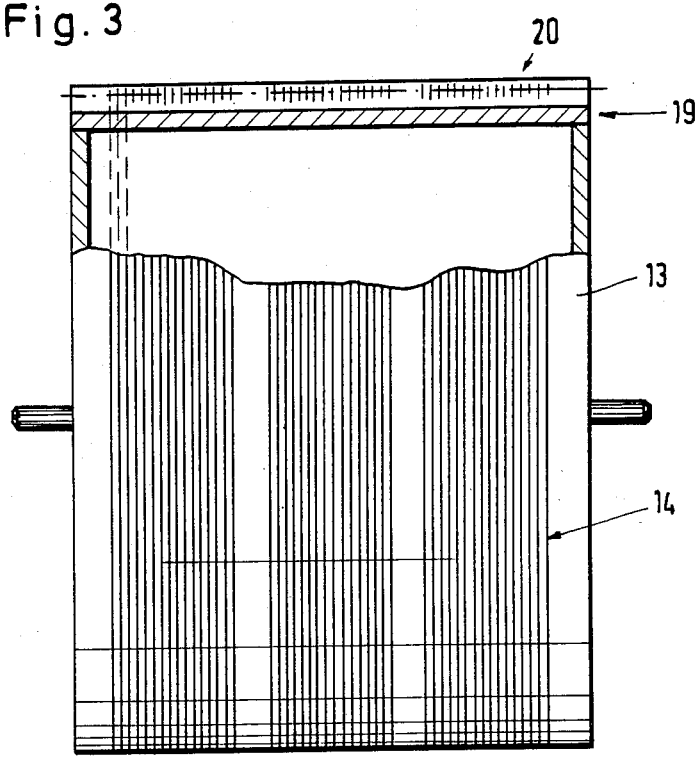
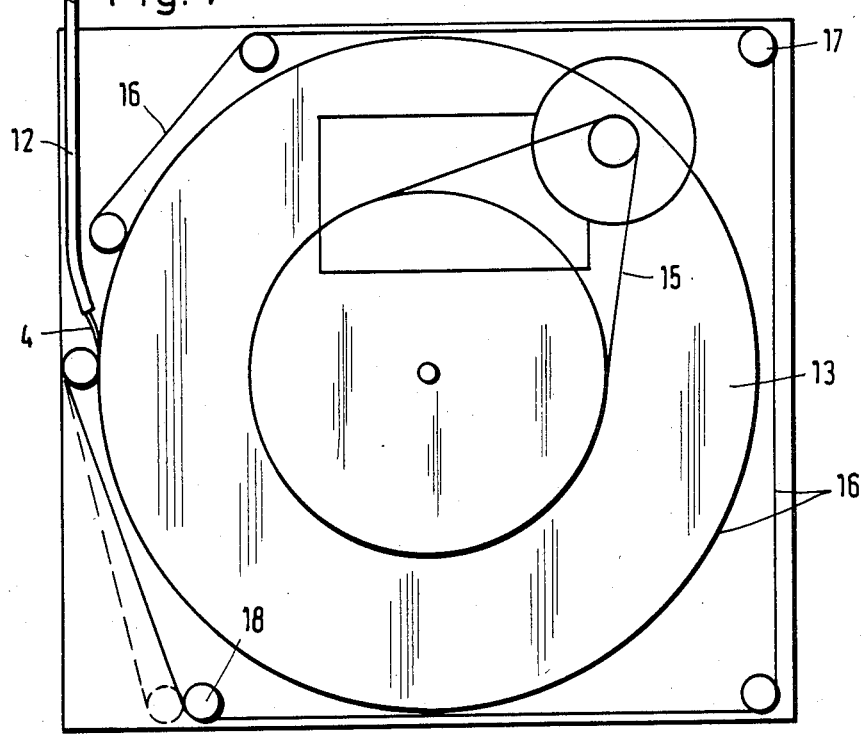

Fig. 8 (B)
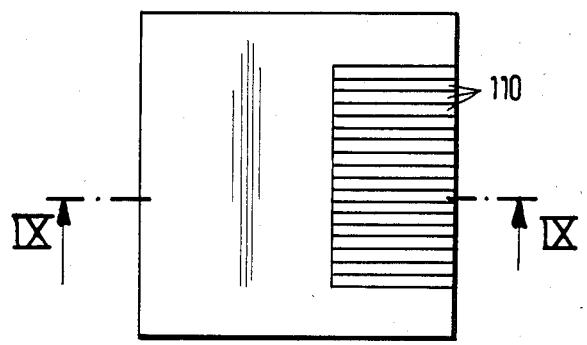
Fig. 9 (IX-IX)
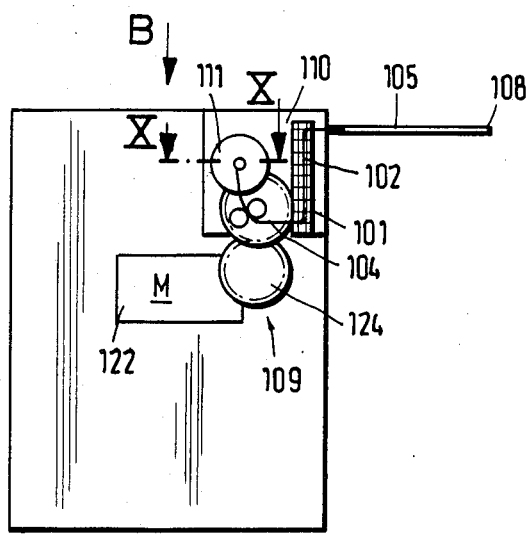
Fig. 10 (X-X)
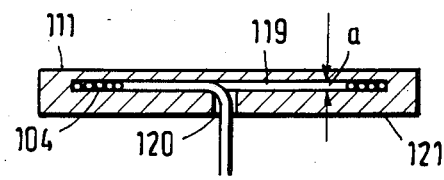

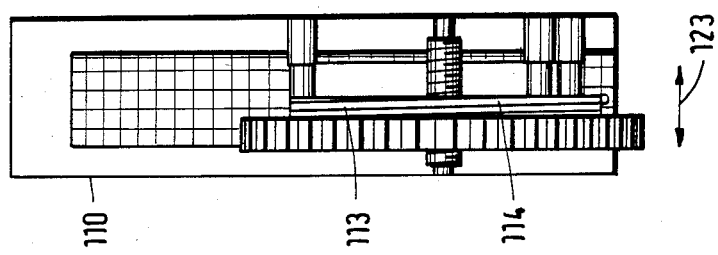
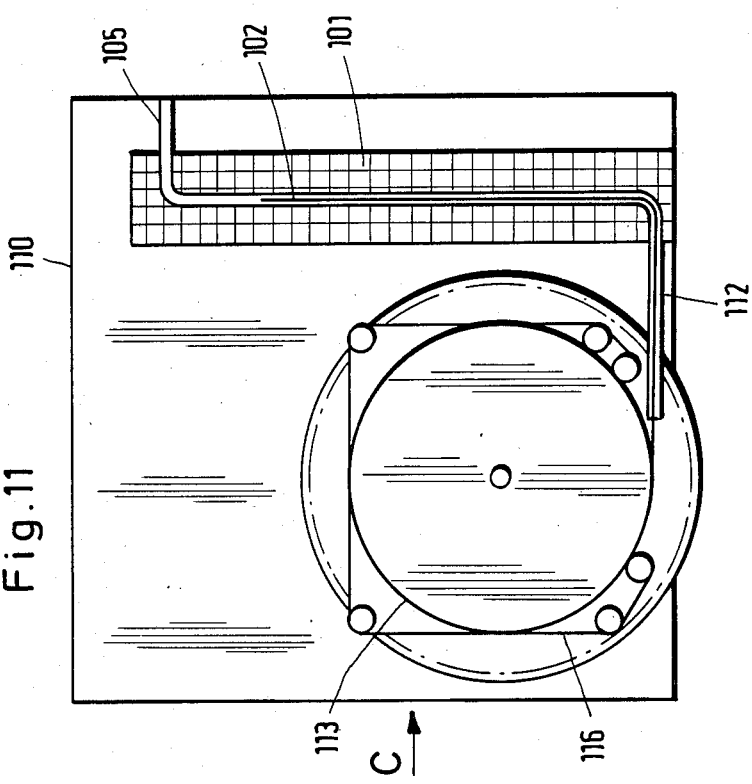

RADIATION TREATMENT APPARATUS

FIELD AND BACKGROUND OF THE INVENTION

The present invention relates to a radiation treatment apparatus according to the preamble of Claims 1 and 6.

Such radiation treatment apparatus are used, in particular, in medical radiotherapy, especially, for instance, for the treatment of tumors. There so-called applicators, i.e. thin hollow needles or plastic flanges are implanted as hollow probes into the target object (the tumor). A radiator holder, for instance a wound spring with spacers and one or more radiation-active zones, is then brought into the hollow probe and thus to the place of treatment (afterloading). When the radiators are not used they must be stored in a radiation shielding container. During the transfer of the radiators from the radiation shielding container into the hollow probe, the operator is exposed to the—even though not excessively strong—radioactive radiation of the radiators. This disadvantage upon the manual insertion of the radiation holder into the hollow probe has been eliminated in an automatically operating afterloading device of the aforementioned type in which the radiation shielding container receives a single radiation holder which, by means of a tube channel switch on the outlet side of the radiation shielding container can be brought into and out of a predeterminable hose which is connected for through-passage with the hollow probe.

This known radiation treatment apparatus has the disadvantage that one can use only a single radiator holder with a single source of radiation present on it and which must be moved within the hollow probe from place of treatment to place of treatment and, after the end of the treatment, moved back within this hollow probe into the radiation shielding container and then, after displacing the hose channel switch, brought into the next hollow probe. This mandatory manner of procedure results in a very long period of treatment during which the object or patient to be treated must be connected to the radiation treatment apparatus. In particular, it is not possible to insert different radiation holders so that two or more predeterminably spaced radiators could be used as necessary on one radiation holder within the individual hollow probes. As a rule, namely, a different number of differently spaced radiation points must be established in the different hollow probes at the place of treatment.

From U.S. Pat. No. 3,861,380 a radiation treatment apparatus of the aforementioned type is known in which a separate drive device is necessary for the insertion and removal of each individual radiator holder—the other radiators therefore remaining in the radiation shielding container; this manner of procedure is possible only with independent drives for the individual radiator holders. In this known radiation treatment apparatus the protection from radiation required for the operating personnel and the patients can of course only be assured if a functional testing of the apparatus without radiators is carried out before each radiation treatment. It is clear that the separate drives of the individual radiators take up a considerable amount of space, so that this known radiation treatment apparatus can be equipped only with comparatively few individually operating radiators (the apparatus must, after all, remain sufficiently small to be portable so that the said test-runs can be carried out in the spaces intended for this).

SUMMARY OF THE INVENTION

Proceeding herefrom, the object of the present invention is to create a radiation treatment apparatus in which, out of the plurality of radiator holders which can be equipped with different numbers of and/or differently spaced sources of radiation, a predeterminable (as desired) number of radiator holders can be introduced simultaneously by means of a drive device, particularly a single drive device, into the corresponding number of hollow probes, while the exposure to radiation of the operating personnel is to be at all times reduced to an unavoidable minimum, particularly also during the radiation treatment. In one practical embodiment of the invention, the radiation shielding container (or containers) is (are) so connected to guide tubes that the drive cables—coming from the drive unit—can be moved axially guided through the guide tubes and thereupon through the radiation shielding container(s) as well as the following flexible hoses. In this way, particularly good guidance of the drive cables is obtained and the first radiation shielding container can be held to a particularly small size since the drive cables can lie very close to each other.

By the invention the advantage is obtained inter alia that any desired combination of the radiator holders provided in the radiation treatment apparatus can be brought simultaneously to the place of treatment, so that the radiation treatment can be carried out simultaneously at all necessary radiation treatment points of the target object. For this there is fundamentally necessary only a single drive unit, since the radiator holders not required at the time for the treatment are guided through their associated flexible hoses into the further radiation shielding container while the radiation holders required at the time for the treatment are guided into the associated hollow probes. In this manner during the period of treatment the sources of radiation which are not required are also stored in shielded manner and the radiation exposure in the environment is reduced to the short interval of time during which the radiator holders pass from the outlet of the first radiation shielding container through the flexible hose into the hollow probe the further radiation shielding container, or vice versa.

In an alternatively proposed radiation treatment the free ends of the hoses can be equipped with hose coupling elements. Such hose couplings can be dispensed with if the hollow probes are firmly connected to the hose ends and therefore form a component part of the cassette element of the invention. Similarly, in this alternative of the invention, it is possible to arrange the hoses with their corresponding hose couplings removably on the radiation shielding container of the cassette element. The storing of the drive cable can be effected alternatively either by means of a winch drum which is mounted turnably on the cassette housing and, in particular, is axially displaceable and on which the drive cable can then be spirally wound, or else by means of a turnable or stationary housing which is arranged on the cassette housing and has a disk-shaped hollow space with a passage opening for the drive cable in one face thereof. The width of the hollow space corresponds approximately to the thickness of the drive cable and the drive cable is adapted to be introduced spirally into the housing by pushing.

A drive drum which receives the drives cables over their entire length of advance permits excellent guidance of the drive cables as well as a space-saving arrangement thereof.

If, in the region between the drive unit and the radiation shielding container(s), the drive cables are arranged between guide grooves of a drive or winch drum and a cover belt which is moveable in the direction of drive, they are dependably guided without frictional losses over the entire length of advance and can have comparatively small dimensions and low flexural rigidity, which, in its turn, favors the required flexibility upon travel within the flexible hoses.

When the drive ends of the drive cables are arranged with axial resiliency in a switch panel, electric switch pulses can exert various control and warning functions before, after and during the movement of the radiator holders. If, for instance, during the travel a radiator, encounters a resistance which does not permit its further travel, then the corresponding drive cable gives off a switch pulse, and thus an error indication for the radiator holder in question. This is advantageous, in particular, when the hose-side hose coupling elements have a detent pawl which shift the free passage as soon as the hose end in question is not properly coupled together with a hollow probe or with the other radiation shielding container; without such a detent pawl and error indication a radiation holder could namely otherwise pass unnoticed into the surrounding atmosphere without any radiation protection. Furthermore, the switch panel of the invention permits the making of contact upon the reaching of the end positions of the radiator holders in the hollow probes or in the other radiation shielding container. In this connection, which radiator holders have moved into the hollow probes and which radiator holders have moved into the radiation shielding container can also be indicated. This is preferably obtained in the manner that the total length of each hose and the hollow probe to be connected with it differs from the total length of the same hose and the free space to be connected with it of the further radiation shielding container by at least the switch path of a limit switch (in the switch panel).

The best possible handling of the hose coupling elements with the smallest possible dimensions of the radiation shielding containers is obtained, according to the invention, in the manner that the corresponding hose coupling elements of the further radiation shielding container are spaced further apart than the flexible hoses emerging from said other radiation shielding container.

The aforementioned components which are to be used in accordance with the invention are not subject to any special exceptional conditions with respect to their size, shape, selection of material or technical design, so that the selection criteria known in their specific field of use can be applied without restriction.

BRIEF DESCRIPTION OF THE DRAWINGS

Further details, features and advantages of the object of the invention will become evident from the following description of the accompanying drawing which shows preferred embodiments of the radiation treatment apparatus of the invention. In the drawing:

FIG. 3 shows a drive drum in radial view, partially in section;

FIG. 4 shows the same drive drum in axial view, corresponding to FIG. 1;

FIG. 8 shows another radiation treatment apparatus as seen from above (seen in the direction B according to FIG. 9);

FIG. 9 shows the same radiation treatment apparatus in a sectional view along the line IX—IX of FIG. 8;

FIG. 10 shows the same radiation treatment apparatus in a section along the line X—X of FIG. 9—in an enlarged fragmentary view;

FIG. 11 shows a cassette unit for a radiation treatment apparatus similar to that shown in FIG. 8; and FIG. 12 shows the same cassette unit, seen in the direction C indicated in FIG. 11.

DETAILED DESCRIPTION OF THE PREFERRED EMBODIMENTS

Figure 1:
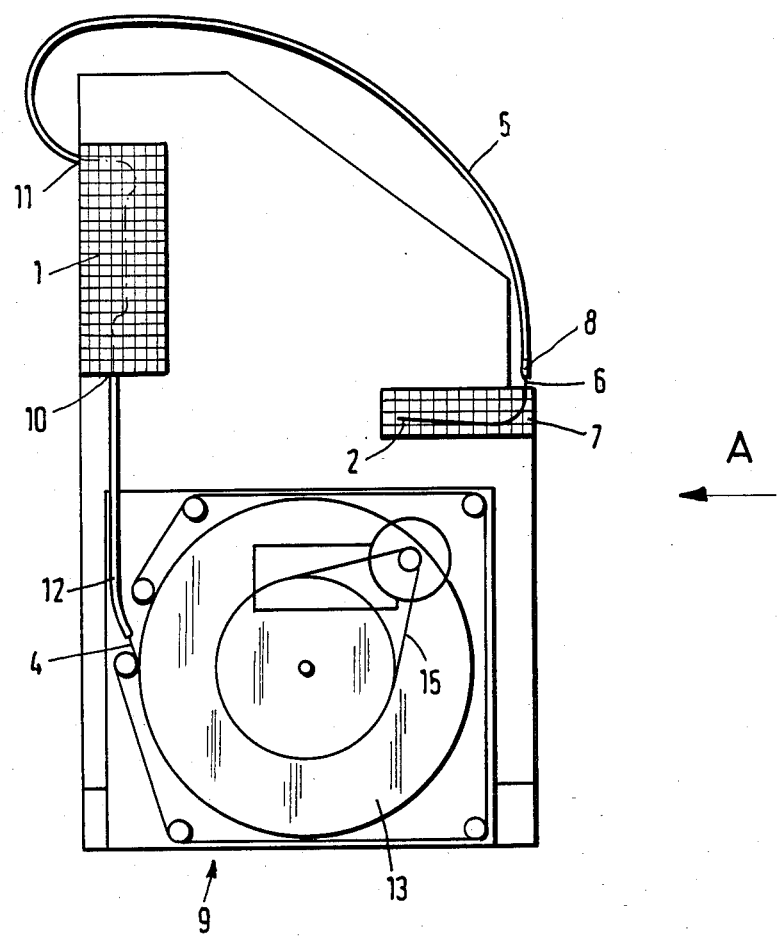
FIG. 1 is a side view of a radiation treatment apparatus.
Figure 7:
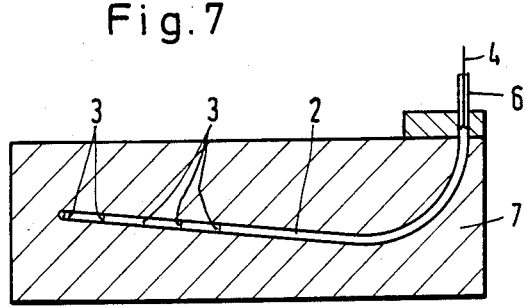
FIG. 7 shows another radiation shielding container with only inlet openings.

The radiation treatment apparatus shown in FIG. 1 consists of a first radiation shielding container 1 (rest container), a plurality of, for example, 48 radiator holders 2 (FIG. 7) containing one or more sources of radioactive radiation 3, known per se, spaced thereon at different distances apart between spacers. Each radiator holder is arranged on the one free end of a corresponding flexible drive cable 4, which cables are guided over paths which are as long as possible and withstand the compressive and tensile stresses which occur without kinking. From the radiation shielding container 1, a number of outlet openings corresponding to the number of radiator holders lead into flexible hoses 5 connected therewith. At its other free end, each of these hoses bears a hose coupling element—not specially shown in the drawing since known per se—for connecting the free end of the hose to a hollow probe—also not shown in the drawing since known per se having a corresponding hose coupling element. This corresponding hose coupling element corresponds to further corresponding hose coupling elements 6 at the inlet openings, corresponding to the number of radiator holders, of another radiation shielding container 7 (intermediate container) which can completely receive, at the same time, all the radiator holders. The free ends 8 of the hoses can thus optionally be detachably connected to the radiation shielding container 7 or to a hollow probe at the place of measurement and they produce through-connections for the radiator holders and the ends of the drive cables.

All drive cables 4 have a common drive unit 9 which is controlled by a single control unit.

The first radiation shielding container 1 has a number of inlet openings 10 and outlet openings 11 which corresponds to the number of radiator holders, between which openings at least a part of the path can be provided with S-shaped guide tubes for the radiator holders and, in particular, the drive cables 4. Further guide tubes 12 connect the inlet openings 10 of the radiation shielding container 1 to the drive unit 9.

The drive unit 9 consists essentially of a drive drum 13 whose circumference is larger than the maximum length of advance and which has radial guide grooves 14 for the individual drive cables 4 (FIG. 3). The drive drum can be turned forward and backward by means of a known belt drive 15.

Figure 5:
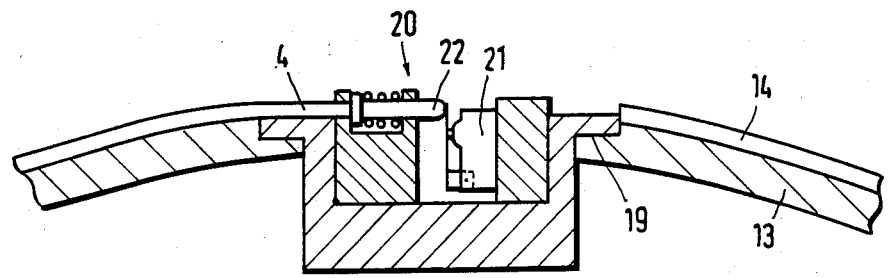
FIG. 5 shows this drive drum in an enlarged radial section.
Figure 6:
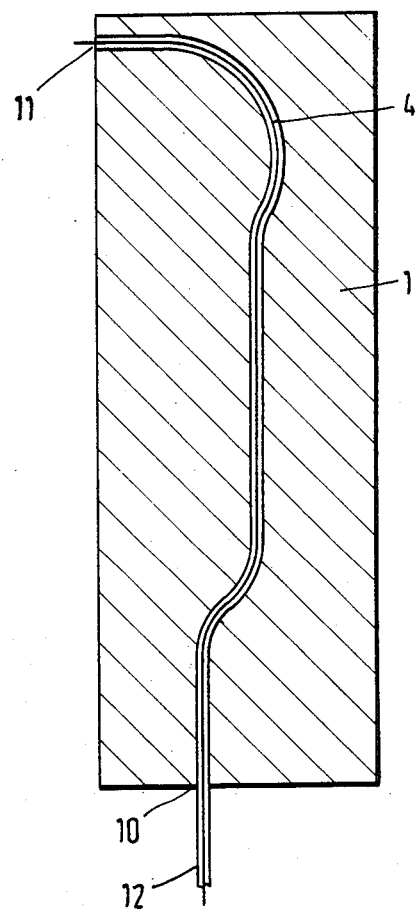
FIG. 6 shows a radiation shielding container with inlet and outlet openings.

A cover belt 16 of the same width as the drive drum 13 is so guided endlessly around the cylindrical wall of the drive drum 13 by means of guide rollers 17 and a tensioning roller 18 that the drive cables 4 rest in the guide grooves 11 even during the rotation and cannot kink. The cover belt 16 covers the entire circumference of the drum except for a very short length of the circumference within which the drive cables 4 lift off from the guide grooves 14 and slide into the free ends of the guide tubes 12. In the periphery of the drive drum 13 there is an axial cutout 19 to receive an axially aligned switch panel 20 having as many proximity or contact switches 21 as there are drive cables 4. The free ends of these drive cables are fastened with axial resiliency in the switch panel 20 and their axially moveable trippers 22 act on the switches 21 (FIG. 5).

Figure 2:
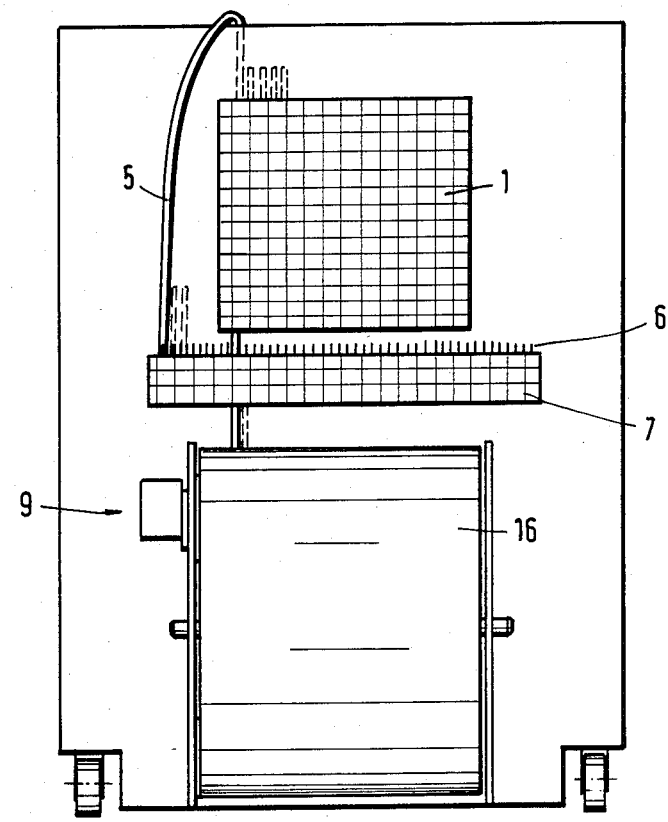
FIG. 2 shows the same radiation treatment apparatus, seen in the direction A in FIG. 1.

As can be noted from FIG. 2, the corresponding hose coupling elements 6 of the further radiation shielding container 7 are spaced apart such a distance alongside of each other on said container that acceptable handling of the coupling elements is assured, while the flexible hoses 5 and the outlet openings 11 on the first radiation shielding container 1 are closer together. Only part of the hoses 5 have been shown in FIG. 2 for the sake of the clarity of the drawing.

Into the radiation treatment apparatus which has been shown merely diagrammatically in FIG. 8, a given plurality of cassette housings 110 can be removably inserted alongside of each other, from above and/or the side. The maximum number of cassette housings which can be inserted alongside of each other is determined by the size of the apparatus. In the normal case, however, less than the maximum possible number of cassette housings are inserted, namely only a number of cassettes equal to the number of radiators required; the other cassette places remain unoccupied.

A cassette housing 110 can be made, for instance, of plastic or metal and be provided with known detent elements so that dependable fixing in place of the cassette housing within the radiation treatment apparatus is possible. Each individual cassette unit receives now in the cassette housing 110 a radiation shielding container 101 and a drive cable 104 having a radiator holder 102 fastened to its end. These three basic elements correspond in their fundamental structure to the radiation shielding container 1, the radiator holder 2 and the drive cable 4 of FIGS. 1 to 7.

In principle, it is possible to arrange a separate motor drive for the drive cable 104 in each cassette housing 110, so that only the supplying of energy is effected by corresponding plug contacts on the cassette housing when the cassette housing is inserted into the radiation treatment apparatus. Preferably however the motor drive lies within the radiation treatment apparatus outside the cassette housing (see FIG. 9), an individual motor being provided for each cassette element or—as preferred—a common drive motor 122 being provided jointly for all cassette elements. This drive motor can either actuate the drive cables 104 at any desired time intervals, which are independent of each other, via individually actuatable couplings or else—as is particularly preferred—the single drive motor 122 can simultaneously drive all drive cables 104 of the cassette units which have been inserted into the radiation treatment apparatus.

The transmission of the power from the drive motor to the drive cables 104 can be effected via interengaging gear wheels, via drive rollers which are in frictional engagement with each other, or via other known coupling members. In this connection, one coupling element, gear wheel or the like is arranged in each case in or on the cassette housing 110 and the mating coupling element, gear wheel or the like is so arranged in the rest of the radiation treatment apparatus that upon the insertion of the cassette element into the radiation treatment apparatus the corresponding coupling elements are functionally connected or connectable.

The drive cable 104 should be capable of being arranged in the smallest possible space within the cassette housing. For this a winch drum 113 (FIGS. 11, 12) is suitable on which the still unextended part of the drive cable is spirally wound. The winch drum 113 is then driven in the manner previously described after the insertion of the cassette housing 110 into the radiation treatment apparatus. In this connection it is advisable to provide for axial displaceability of the winch drum 113 as indicated by the arrow 123 in FIG. 12, so that the drive cable can be inserted, without bending, into the adjoining guide tube 112. A covering of the winch drum 113 by a covering belt similar to what has been described in connection with FIGS. 1 to 5 can be provided.

Another possibility for the arrangement of the unextended end of the drive cable consists of a housing 111, as shown in FIGS. 9 and 10, which has a preferably diskshaped hollow space 119, whose width a (inside width) is only slightly greater than the thickness of the drive cable 104. This housing 111 may—corresponding to the shape of its hollow space—be a flat cylinder which is driven by a drive roller 124, the drive motor 122 driving the drive roller 124. This drive roller 124 may act simultaneously on the housing 111 of all cassette elements inserted into the radiation treatment apparatus. For the emergence of the drive cable 104 there is a passage opening 120 in the center of the face 121 of the housing 111. The unextended end of the drive cable 104 lies spirally within the hollow space 119 and its free end is fixed there; thus the turning of the housing 111 in the manner described above leads to the moving in or out of the drive cable 104. This type of drive-cable actuation is of course extremely diversified and therefore not for use exclusively in the radiation treatment apparatus of the invention.

The particular advantage of the cassette elements of the invention is that the radiators to be used need no longer be replaced by the operating personnel but can rather form an integral part of the cassette element. When the radiation treatment apparatus of the invention is used it is therefore no longer necessary to make do with a single type of radiator or determine in final manner the radiators with which the individual radiator holders are to be equipped already at the time of the manufacture of the apparatus. Furthermore, a coupling can be dispensed with between radiator holder and drive cable.

We claim:

1. A radiation treatment apparatus comprising
    a first radiation shielding container comprising a rest container having a plurality of first openings,
    a plurality of flexible hoses connected to said openings respectively,
    a plurality of drive cables extending through said flexible hoses respectively, a plurality of radiator holders connected to said drive cables respectively, said radiator holders are axially insertable and removable from said openings by means of a respective of said drive cables through a respective of said flexible hoses, a common single drive means connected to all of said drive cables for joint movement of all said drive cables and therewith for joint insertion and joint removal of said radiator holders into and from said openings, respectively, via said drive cables, a second radiation shielding container comprising an intermediate container having a plurality of second openings for selectively receiving respective of said radiation holders, a plurality of means comprising hose coupling elements for producing detachable through-connections of free ends of said flexible hoses, respectively, selectively to one of a respective of said second openings and a respective hollow probe for treatment, all of said plurality are the same in number, said drive means further for simultaneously inserting said radiation holders which are selected for treatment into the respective hollow probes and for simultaneously inserting said radiation holders which are not selected for treatment into the respective second openings, whereby the radiator holders not selected at the time for treatment are guided through said respective flexible hoses into the respective second openings in the second radiation shielding container while the radiation holders selected at the time for treatment are guided into the respective hollow probes.

2. The radiation treatment apparatus according to claim 1, wherein
said common single drive means comprise a drive drum, the circumference of which is larger than a maximum length of advance of the cables respectively.

3. The radiation treatment apparatus according to claim 2, wherein
said drive cables have drive-side ends arranged with axial resiliency in a switch panel.

4. The radiation treatment apparatus according to claim 1, wherein
the total length of each said hose and the respective hollow probe to be connected therewith differs from the total length of said hose and free space of the second opening to be connected therewith of the second radiation shielding container by at least a switch part of a limit switch.

5. The radiation treatment apparatus according to claim 1, wherein
said means include corresponding hose coupling elements of the second radiation shielding container which are spaced further apart than the flexible hoses extending out of the first radiation shielding container.

6. A radiation treatment apparatus comprising
at least one radiation shielding container having a plurality of openings,
a plurality of flexible hoses connected to said openings respectively,
a plurality of drive cables extending through said flexible hoses respectively,
a plurality of radiator holders connected to said drive cables respectively, said radiator holders are axially insertable and removable from said openings by means of a respective of said drive cables through a respective of said flexible hoses, a common single drive means connected to all of said drive cables for joint movement of all said drive cables and therewith for joint insertion and joint removal of said radiator holders into and from said openings respectively, via said drive cables, a separate cassette housing in which each said drive cable together with a respective of said radiator holders and a radiation shielding container is arranged, and a freely selectable number of said cassette housings are removably inserted into the radiation treatment apparatus in such a manner that all the drive cables of all the inserted cassette housings are connected for simultaneously driving to the drive means of the radiation treatment apparatus.

7. The radiation treatment apparatus according to claim 6, wherein
said drive means includes a winch drum mounted for rotation on the cassette housing and said drive cable is spirally windable onto said winch drum.

8. The radiation treatment apparatus according to claim 6, wherein
a housing is arranged on the cassette housing and has a disk-shaped hollow space with a passage opening for the drive cable in one face thereof, said hollow space has a width corresponding approximately to the thickness of the drive cable, and the drive cable is spirally insertable by pushing into said hollow space.

9. The radiation treatment apparatus according to claim 2 further comprising
a cover belt between said drive means and at least one of said radiation shielding containers,
said driving drum is formed with guide grooves, said drive cables are arranged between said guide grooves of the driving drum and said cover belt which is movable in a driving direction.

10. The radiation treatment apparatus according to claim 1 further comprising
a plurality of guide tubes,
the first radiation shielding container is connected to said guide tubes such that the respective drive cable is guided axially movably through the guide tubes and then through the first radiation shielding container and the respective flexible hoses.

11. The radiation treatment apparatus according to claim 6 further comprising
a plurality of guide tubes,
the first radiation shielding container is connected to said guide tubes such that the respective drive cable is guided axially movably through the guide tubes and then through the first radiation shielding container and the respective flexible hoses.

12. The radiation treatment apparatus according to claim 7 further comprising
a cover belt between said drive means and at least one of said radiation shielding containers,
said winch drum is formed with guide grooves, said drive cables are arranged between said guide grooves of the winch drum and said cover belt which is movable in a driving direction.

13. The radiation treatment apparatus according to claim 1, wherein
each said second openings has only one inlet, and
each said first openings has a separate inlet and outlet.

* * * * *